United States Patent [19]
Hübner

[11] Patent Number: 4,703,555
[45] Date of Patent: Nov. 3, 1987

[54] METHOD OF MAKING A CATALYTIC-BURNING SENSOR

[76] Inventor: Hans-Jörg Hübner, Pfarrer-Kneipp-Str. 9, D-4600 Dortmund 1, Fed. Rep. of Germany

[21] Appl. No.: 750,529

[22] Filed: Jun. 28, 1985

Related U.S. Application Data

[63] Continuation-in-part of Ser. No. 730,792, May 6, 1985.

[30] Foreign Application Priority Data

May 5, 1984 [DE] Fed. Rep. of Germany ....... 3416657

[51] Int. Cl.[4] .............................................. H05B 3/00
[52] U.S. Cl. ....................................... 29/611; 338/34; 338/13
[58] Field of Search ............... 338/34, 13, 14; 29/570, 29/611, 620; 228/141.1, 159, 162; 219/56.21, 56.22

[56] References Cited

U.S. PATENT DOCUMENTS 4,171,477 10/1979 Funari ............................ 219/56.21
4,397,702 8/1983 Klein et al. ....................... 29/592 E

*Primary Examiner*—E. A. Goldberg
*Assistant Examiner*—M. M. Lateef
*Attorney, Agent, or Firm*—Browdy and Neimark

[57] ABSTRACT

A catalytic-combustion sensor has a rigid support having a flat support face, a metallic resistance-type heater film flatly adhered to the support face, and a catalyst film flatly adhered in heat-transmitting connection to the heater film. The heater element is made of platinum or gold and the catalyst film is made of a platinum-group compound such as a palladium-, platinum, rhodium-, or iridium-compound, in an arrangement used to detect methane, although different materials can be used for other gases such as propane or butane. Normally a diffusion-blocking layer overlies the catalyst film. The heater film is a strip following a nonstraight, normally meandering, path on the support face and support is a rigid bar having a back face opposite to the support face and formed thereon in registration with the nonstraight heater film with a rearwardly open groove that reduces the thickness of the bar at the heater film. The thickness of the support is reduced to the minimum necessary to have sufficient rigidity to keep the support from breaking up when in use and to reduce the thermal mass of the support in the region of the heater strip.

13 Claims, 4 Drawing Figures

METHOD OF MAKING A CATALYTIC-BURNING SENSOR

CROSS-REFERENCE TO RELATED APPLICATION

This application is a continuation-in-part of copending patent application Ser. No. 730,792 filed May 6, 1985.

FIELD OF THE INVENTION

The present invention relates to a sensor for catalytic burning. More particularly this invention concerns such a sensor which uses the catalytic combustion of gases like methane and a method of making this sensor.

BACKGROUND OF THE INVENTION

The catalytic combustion of gases such as methane ($CH_4$) is typically accomplished with a metallic resistance-type heating element that heats a catalyst that is typically covered by a layer of material to protect it, for example, from sulfur dioxide. The heating element is normally made of a noble metal such as platinum or gold and the catalyst is from group VII, that is usually a palladium, platinum, rhodium, or iridium alloy.

As described in British patent document No. 2,083,630 it is known to use a pellistor as sensor in a process which cataytically burns methane in an oxygen-containing gas, normally air. The catalytic combustion of methane generates temperatures of about 800° K. Other hydrocarbons such as butane or propane are typically combusted at lower temperatures of around 500° K. The catalytic combustion can serve to rid an exhaust gas of a harmful component, or can be used merely as will be described below in a laboratory or industry setting to determine the concentration of the hydrocarbon gas at a location, for instance in a process stage or smokestack.

The resistance-type electrical heater heats the catalyst material so as to trigger the catalytic combustion. This heater serves simultaneously to detect whether catalytic combustion is taking place and simultaneously therefore determines whether any methane or other gas being detected is present. In the absence of any combustion the temperature of the heater and catalyst will remain uniform, presuming uniform energization of the heater and uniform throughput of gas. When methane enters the system, however, catalytic combustion takes place and the temperature of the catalyst and of the heater increases due to this secondary input of heat energy from the exothermic catalytic combustion. As the temperature of the resistive heater increases so does its resistance, causing a corresponding and measurable decrease in current flow, once again presuming unchanging energization voltage. The change in resistance in ohms or the change in current in amperes therefore is fairly directly proportional to the concentration of the gas being catalytically combusted, making it possible to accurately measure such concentration.

A standard platinum wire of the type used in such a sensor has, unfortunately, a very small change in resistance when the temperature changes by, say, 0.003/°K., as can occur when a quantity of methane appears that should be measured. Gold and palladium, which are also usable as resistance-type heating elements in burners for methane and similar hydrocarbon gases, also do not change in resistance greatly with small temperature changes. Thus it is necessary to use complicated and expensive monitoring equipment capable of sensing tiny variations in resistance and converting them into usable gas-concentration readings.

Such devices therefore are quite costly to manufacture. They are also fairly delicate because the wires are made very thin to spare the costly noble metals that must be used for the necessary catalytic reaction. Finally they typically operate sluggishly, responding slowly because it takes some time for the exothermic catalytic combustion to heat up the thermal mass of the heater and catalytic body carried on it.

OBJECTS OF THE INVENTION

It is therefore an object of the present invention to provide an improved sensor.

Another object is the provision of such a sensor which operates by the above-described catalytic-combustion method and which overcomes the above-given disadvantages of high cost, fragility, and slow response.

SUMMARY OF THE INVENTION

A catalytic-combustion sensor according to the invention has a rigid support having a flat support face, a metallic resistance-type heater film flatly adhered to the support face, and a catalyst film flatly adhered in heat-transmitting connection to the heater film. The heater film is made of platinum or gold and the catalyst film comprises a platinum-group compound such as a palladium-, platinum-, rhodium-, or iridium-compound, in an arrangement used to detect methane, although different materials can be used for other gases such as propane or butane. Normally an at least partially semipermeable diffusion-blocking layer overlies the catalyst film.

The application of such thin or thick films to the rigid substrate of the support is an extremely simple operation that is greatly cheaper than the production of the necessary noble-metal heating wire. In addition the resultant rigid heater is extremely simple to mount, transport, and generally inexpensive both to make and use.

According to another feature of this invention the heater film is a strip following a definite path on the support face. Preferably this path is a nonstraight, normally meandering path. This increases the length of the heater film and its resistance without increasing the length of the rigid support.

According to another feature of this invention the support is a rigid bar having a back face opposite to the support face and formed thereon in registration with the nonstraight heater film with a rearwardly open groove that reduces the thickness of the bar at the heater film. The thickness of the support is reduced to the minimum necessary to have sufficient rigidity to keep the support from breaking when in use, to reduced the thermal mass of the support in the region of the heater strip. This correspondingly reduces the response time of the sensor. In addition the thick webs of the support, which have not been machined away, make mounting the sensor relatively simple, much more so than a delicate platinum-wire coil.

Such an arrangement can also have a temperature sensor applied inside the groove to the back face of the support directly underneath the heater strip. This element can be a thermoelement, a temperature-sensitive resistor, a thermistor, a transistor, or a diode. Thus the measuring function is divorced from the heating element, but since the temperature sensor is only separated from the heating strip by a very thin web, it will accurately be able to determine the temperature at the heating strip.

According to a feature of this invention the support has a thickness measured perpendicular to the support face that is between 0.05 mm and 0.2 mm at the groove and between 0.3 mm and 1.0 mm offset from the groove. In addition heat flow from the thin groove region to the balance of the support is reduced when the support is formed to each side of the nonstraight heater strip with a row of transversely throughgoing holes. It is also possible to provide thermally insulating elements or bumps that separate the heater strip from the support face of the support.

It lies within the scope of this invention for the support to be of an insulating material, for instance aluminum oxide or another temperature-resistant ceramic or material. In fact the support can be a semiconductor such as monocrystalline silicon. In this case there should be an insulating layer between the support and the heater element. Furthermore the support can also form part of or carry an integrated circuit. This last-mentioned possibility allows the sensor circuit and other related electronic elements to be built right into the sensor so that manufacturing costs can be held very low.

According to another feature of this invention the support is of a metal in which case the sensor has an insulating layer between the support and the heater element. Anyway, the insulating layer can be silicon dioxide ($Si0_2$), silicon nitride ($Si_3N_4$), or glass. It can have a thickness of between 0.001 mm and 0.1 mm (1 micron to 100 micron).

The heater film of this invention has a thickness of between 0.0005 mm and 0.01 mm (0.5 micron to 10 micron). In addition the catalyst film has a thickness of between 0.0001 mm and 0.01 mm (0.1 micron to 10 micron). The diffusion-blocking layer overlying the catalyst film has a thickness of between 0.001 mm and 0.01 mm (1 micron to 10 micron). Thus the structure above the support face has a thickness of at most 1.02 mm, plus the thickness of any insulating layer between the heater strip and the support face.

The method of this invention basically comprises the steps of bonding the heater film to the support face of the rigid support and thereafter reducing the thickness of the rigid support to a minimum by machining the opposite face of the support. This allows a rigid and easy-to-handle support bar to be worked with for the application of the delicate and very thin heater film. A subsequent thickness reduction then reduces the thermal mass.

According to another feature of the method of this invention after bonding the heater film to the support and before machining the opposite face of the support the catalyst film is bonded to the support over the heater film. Then a diffusion protective layer is bonded in place over the catalyst film. This protective layer is permeable to the gas being detected and to oxygen, but not to harmful substances like hexamethyldisiloxane or sulfur dioxide. Such layers which pass certain substances and block others are well known in the art.

According to a further feature of the method of this invention the heater film may be bonded to the support face in a nonstraight preferably meandering path. This allows for the further step of machining in the opposite face of the support a groove with the desired minimum thickness in registration underneath the heater strip. According to this important feature of the invention the entire assembly is left as a fairly rigid bar while reducing the thermal mass at the particularly critical region underneath the heater strip.

DESCRIPTION OF THE DRAWING

The above and other features and advantages will become more readily apparent from the following, reference being made to the accompanying drawing in which.

SPECIFIC DESCRIPTION

Figure 1:
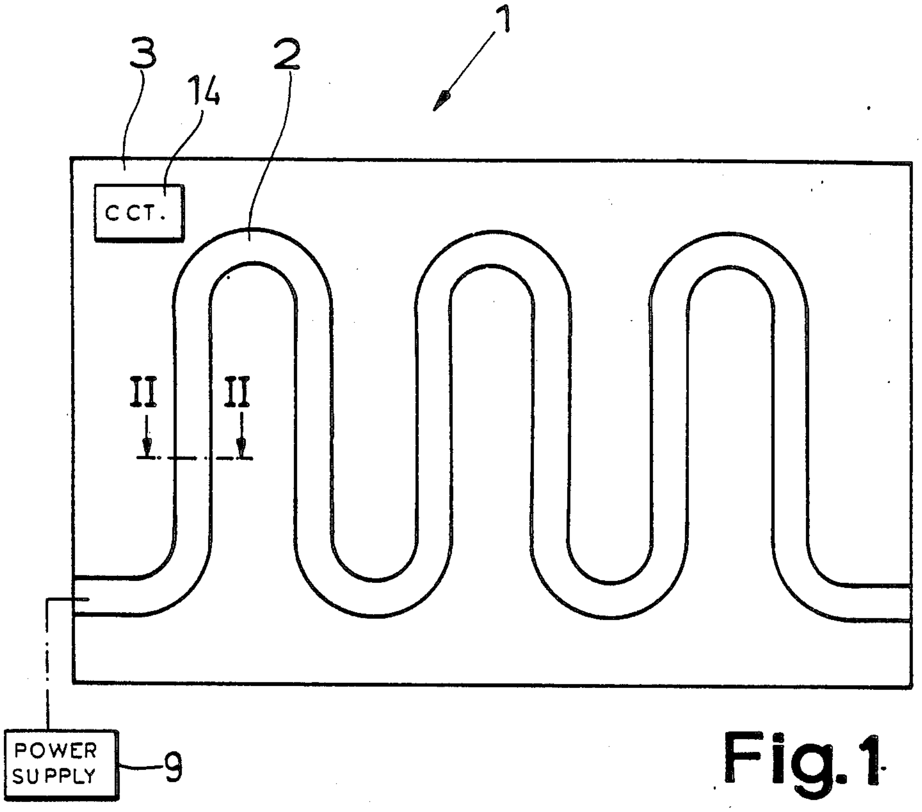
FIG. 1 is a partly diagrammatic and not-to-scale top view of the sensor according to the invention.
Figure 2:
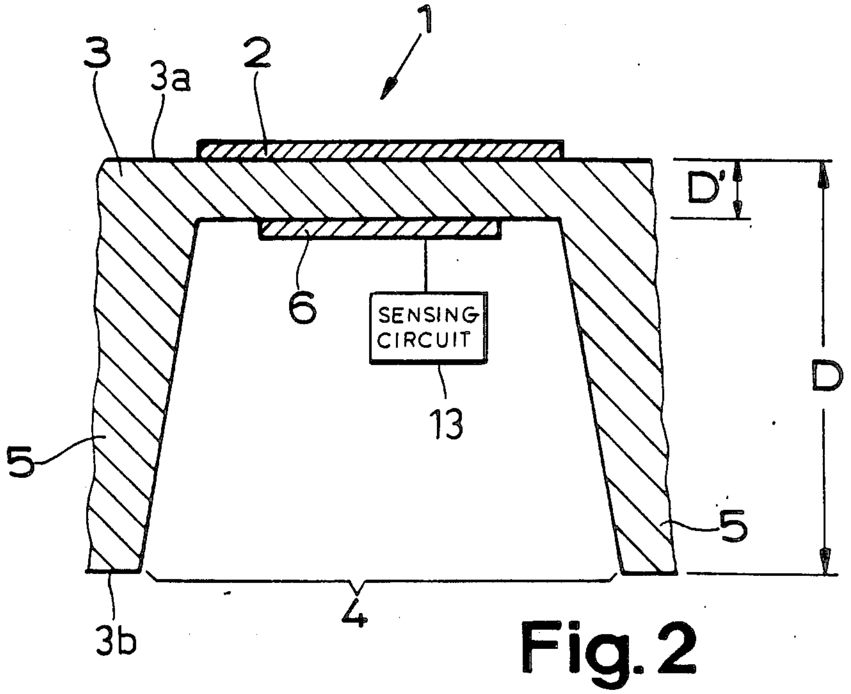
FIG. 2 is a large-scale section taken along line II—II of FIG. 1.

As seen in FIGS. 1 and 2 a sensor 1 according to this invention is basically formed of a rigid support bar 3 to which is applied a meandering strip 2 of a resistive-heating metal, here of platinum. In use, a power supply 9 is connected to the ends of the strip 2 to cause it to heat up.

Figure 4:
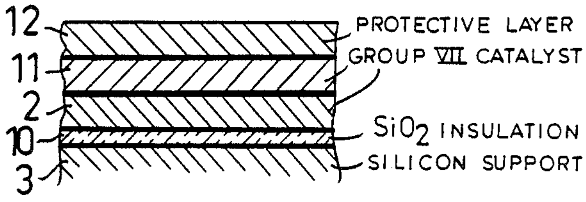
FIG. 4 is a large scale but not-to-scale section taken along line IV—IV of FIG. 2.

In reality as shown in FIG. 4 also, the support body 3 is made of monocrystalline silicon and has a planar upper or front face *3a* provided with a coating 10 of insulating material such as silicon dioxide. This coating 10 carries the meander strip 2 of the resistive heating element 2 to which is applied another thin- or thick-film layer 11 of the catalyst, here a palladium compound. On top of the layer 11 a protective layer 12 can be provided to prevent, for example, any sulfur dioxide in the gas being sampled from eroding the catalyst layer 11.

In this arrangement the $SiO_2$ insulation layer 10 has a thickness of about 2 micron. The heater layer 2 is about 1 micron thick, the catalyst layer 11 about 0.5 micron thick, and the protective layer 12 some 2 micron thick. This gives the entire stack of layers 10, 2, 11, and 12 an overall thickness of about 5.5 micron.

The support 3 as shown in FIG. 2 is made from a rigid bar having to start with a thickness D of 0.65 mm. To this body the insulating layer 10 and meander strip 2 are applied in any of several standard industry techniques. The application is fairly simple because the thickness D makes the body 3 fairly rigid and easy to handle.

Once the resistive strip 2 has been applied the back face *3b* of the support 1 is machined out at a meander groove 4 directly behind or, as seen in the drawing, underneath the meander strip 2. This reduces the support thickness at the resistive-heater strip 2 to D', here about 0.09 mm, which is about one-seventh of the thickness D. This reduction in thickness is a simple machining operation that in no way endangers the strip 2 on the front face of the heater support 3. Even with the groove 4 machined in the body 3, the body 3 is relatively rigid and strong, as it still has full-thickness webs 5 outside the groove 4.

The reduction in thickness at the strip 2 reduces the thermal mass at the heater 2. In addition it makes it possible to mount a resistance-type sensor strip 6 connected to a sensing circuit 13 in the floor of the groove 4 following the same meander path as the strip 3 and responding rapidly to the temperature changes on the front of the body 3.

Figure 3:
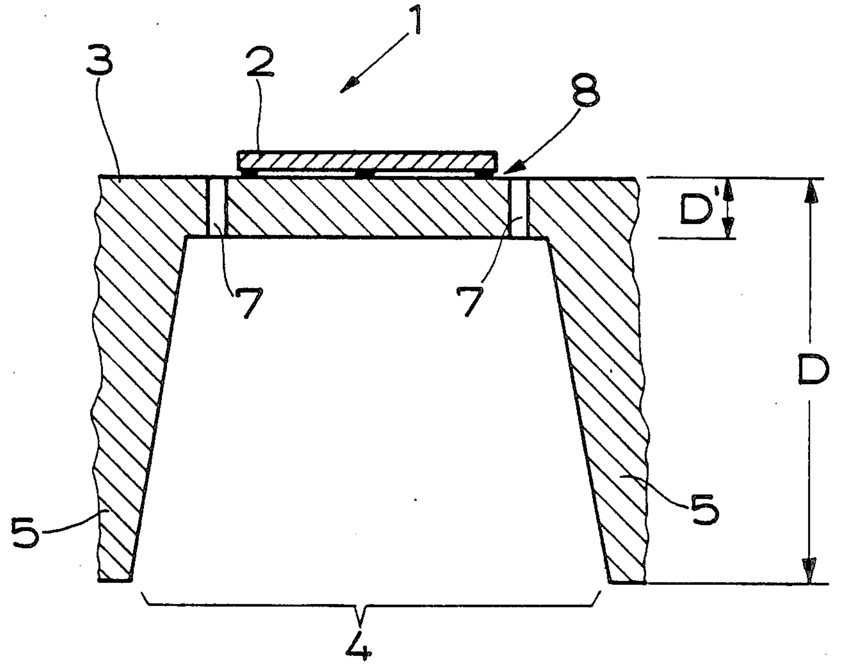
FIG. 3 is a view like FIG. 2 of another arrangement according to the invention.

Of course it is possible to put the layers 11 and 12 on before machining out the groove 4 and the body 3 can itself be the base for an integrated or printed circuit 14. Similarly it is possible as shown in FIG. 3 to form respective series of insulating holes 7 along both edges of the meander strip 2 and to hold same out by discreet insulating bumps 8. The holes 7 reduce the thermal coupling between the portion of the body 3 underneath the heater 2 and the rest of the body 3. In this arrangement the sensing circuit 13 would be connected to the strip 2 directly and the strip 6 would be dispensed with, for very fast and virtually inertia-free reaction to temperature changes which, as described above, themselves are indicative of the presence of methane.

It would of course be possible to substitute catalysts and other materials for reaction to the catalytic combustion of other hydrocarbons, as for instance butane or propane, without leaving the scope of this invention.

The sensor can be used in my device in which the presence of concentration of methane is detected or measured by the catalytic combustion of methane.

What is claimed is:

1. A method of making a catalytic-combustion sensor comprising:

a rigid support having a flat support face;

a metallic resistance-type heater film flatly adhered to the support face; and a catalyst film flatly adhered in heat-transmitting connection to the heater film, the method comprising the steps of:

bonding the heater film to the support face of the rigid support; and thereafter reducing the thickness of the rigid support from between 0.3 mm and 1.0 mm to between 0.05 mm and 0.2 mm by exclusively machining the face of the support at an area corresponding to and opposite said heater film.

2. The method defined in claim 1, further comprising the step, after bonding the heater film to the support and before machining the opposite face of the support, of bonding the catalyst film over the heater film.

3. The method defined in claim 2, further comprising the step, after bonding the catalyst film over the heater film and before machining the opposite face of the support, of bonding a diffusion protective layer over the catalyst film.

4. The method defined in claim 1 wherein the heater film is bonded to the support in a nonstraight preferably meandering path, the thickness of the support being reduced by machining in the opposite face of the support a groove in registration underneath the heater strip.

5. The method defined in claim 1, further comprising the step of forming the support to each side of the heater film with a row of transversely throughgoing holes thermally separating the support at the heater film from the rest of the support.

6. The method defined in claim 1, further comprising the step of providing thermal insulating spacers between the heater film and the support.

7. The method defined in claim 1 wherein the support is of a semiconducting material, the method further comprising the step of providing an insulating layer between the support and the heater film.

8. The method defined in claim 1, further comprising the step of mounting an integrated circuit on the support.

9. The method defined in claim 1 wherein the support is of a metal, the method further comprising the step of providing an insulating layer between the support and the heater film.

10. The method defined in claim 1, further comprising the step of providing an insulating layer of silicon oxide, silicon nitride, or glass between the support and the heater film.

11. The method defined in claim 1, further comprising the step of providing a temperature sensor on the opposite face of the support directly underneath the heater film.

12. A catalytic-combustion sensor made according to the method of claim 1.

13. The sensor defined in claim 12 wherein the heater film is made of platinum or gold and the catalyst film comprises a platinum-group compound including palladium, platinum, rhodium, or iridium.

* * * * *